United States Patent [19]
Schwirten et al.

[11] Patent Number: 4,568,653
[45] Date of Patent: Feb. 4, 1986

[54] WORKING UP OF HYDROFORMYLATION OR CARBONYLATION REACTION MIXTURES

[75] Inventors: Kurt Schwirten, Ludwigshafen; Rudolf Kummer, Frankenthal; Wolfgang Richter, Ludwigshafen, all of Fed. Rep. of Germany

[73] Assignee: BASF Aktiengesellschaft, Fed. Rep. of Germany

[21] Appl. No.: 222,893

[22] Filed: Jan. 6, 1981

Related U.S. Application Data

[63] Continuation of Ser. No. 52,722, Jun. 28, 1979, abandoned.

[30] Foreign Application Priority Data

Jul. 29, 1978 [DE] Fed. Rep. of Germany ....... 2833469

[51] Int. Cl.$^4$ ...................... B01J 31/40; C07C 45/50; C07C 51/14; C07C 67/38
[52] U.S. Cl. ......................................... 502/34; 502/22; 502/35; 560/233; 562/522; 568/454; 568/909
[58] Field of Search .................... 252/411 R, 431 P; 260/429 R; 568/454; 502/22, 34, 35

[56] References Cited

U.S. PATENT DOCUMENTS

| | | | |
|---|---|---|---|
| 3,369,050 | 2/1968 | Greene | 568/454 |
| 3,547,964 | 12/1970 | Olivier | 568/909 |
| 3,856,832 | 12/1974 | Keblys | 560/233 |
| 3,969,196 | 7/1976 | Zosel | 203/49 |
| 4,041,082 | 8/1977 | Omada et al. | 568/454 |
| 4,166,773 | 9/1979 | Higley et al. | 568/454 |
| 4,250,331 | 2/1981 | Shimshik | 562/485 |

FOREIGN PATENT DOCUMENTS

| | | | |
|---|---|---|---|
| 1493190 | 1/1973 | Fed. Rep. of Germany | 203/49 |
| 2438847 | 2/1975 | Fed. Rep. of Germany | 568/454 |
| 2853065 | 6/1980 | Fed. Rep. of Germany | 502/34 |
| 2054394 | 2/1981 | United Kingdom | 502/34 |

*Primary Examiner*—P. E. Konopka
*Attorney, Agent, or Firm*—Keil & Weinkauf

[57] ABSTRACT

Reaction mixtures which are obtained on hydroformylation or carbonylation of olefinically unsaturated compounds and which contain dissolved non-volatile complex compounds of metals of group VIII of the periodic table are worked up by a method wherein the products, after distillative removal of low-boiling constituents alone, or of these constituents plus a part of the high-boiling residue, or a part of the high-boiling residue after distillative removal of the desired products, are or is extracted with carbon dioxide, a $C_2$-$C_4$-paraffin, a $C_2$-$C_4$-olefin or a normally gaseous halohydrocarbon at above the critical temperature and above the critical pressure of these (extractant) compounds.

5 Claims, No Drawings

WORKING UP OF HYDROFORMYLATION OR CARBONYLATION REACTION MIXTURES

This is a continuation of application Ser. No. 052,722, filed June 28, 1979, now abandoned.

The present invention relates to a novel process for working up the reaction mixtures which are obtained on hydroformylation or carbonylation of olefinically unsaturated compounds and which contain dissolved nonvolatile complex compounds of metals of group VIII of the periodic table.

The hydroformylation or carbonylation of olefinically unsaturated compounds with carbon monoxide and, respectively, hydrogen or water or alcohols, in the presence of carbonyl complex compounds of metals of group VIII of the periodic table at elevated temperatures and under superatmospheric pressure results, as is generally known, in reaction mixtures which can be worked up by various methods. If volatile carbonyl complexes, for example dicobalt-octacarbonyl, are used, it is necessary to destroy these before distilling the products—namely aldehydes and alcohols in the case of hydroformylation or acids and esters in the case of carbonylation—from the crude mixture, since these products would otherwise become contaminated by the heavy metals.

If on the other hand complex compounds are used in which a part of the carbonyl groups is replaced by other ligands, for example triphenylphosphine, it offers, inter alia, the advantage that the products can be distilled off directly from the crude mixture. Such distillation leaves a residue of high-boiling organic compounds, which contains the unchanged catalysts in solution and which can therefore be recycled, in this form, to the synthesis step, since the high-boiling compounds do not interfere with the hydroformylation or carbonylation reaction.

However, it is a disadvantage of this method that the amount of the residue naturally increases constantly, and therefore the residue must from time to time be worked up completely. Simply to discard it would be uneconomical, particularly when it contains noble metal catalysts such as rhodium complexes, quite apart from the fact that for environmental reasons such disposal would not be possible.

According to the process of U.S. Pat. No. 3,547,964, the hydroformylation residue is treated with aqueous peroxides, whereby the complex compounds of the metals are converted to their salts, which accumulate in the aqueous phase. The organic phase is combusted, whilst the heavy metal salts contained in the aqueous phase can be reconverted, by means of carbon monoxide and other ligand compounds, for example triphenylphosphine, into the active form of the carbonyl complexes.

In another process (German Laid-Open Application DOS No. 2,438,847) the residue is combusted, after which the combustion products are passed through water. This retains the heavy metals, which can subsequently be recycled to the catalyst regeneration step.

These and similar processes, which are based on chemical treatment of the residue and of the catalysts, however require expensive equipment, present numerous technological problems and are economically unsatisfactory, if only because the regeneration of the catalyst must be preceded by its destruction. However, it is frequently not only the processing of the high-boiling residue which presents technical problems, but even the isolation of the products of the process. If the latter are themselves high-boiling even under reduced pressure, as in the case of higher aldehydes, alchols, acids or esters, the catalysts may decompose to the metals at the distillation temperature, even if they contain stabilizing ligands, such as tertiary phosphines. If the metals can be recovered at all and do not deposit on the walls of the distillation apparatus, they must, before re-use, be reconverted, by involved methods, to the active catalysts.

German Published Application DAS No. 1,493,190 discloses in general terms that to separate mixtures of compounds, gases in the supercritical state may be used for extraction.

It is an object of the present invention to provide a novel process for working up the catalyst-containing reaction mixtures, which does not suffer from the stated disadvantages.

We have found that reaction mixtures which are obtained on hydroformylation or carbonylation of olefinically unsaturated compounds and which contain dissolved nonvolatile complex compounds of metals of group VIII of the periodic table can be worked up economically and without destroying the complex compounds by a method wherein the products, after distillative removal of low-boiling constituents alone, or of these constituents plus a part of the high-boiling residue, or a part of the high-boiling residue after distillative removal of the desired products, are or is extracted with carbon dioxide, a $C_2$–$C_4$-paraffin, a $C_2$–$C_4$-olefin or a normally gaseous halohydrocarbon at above the critical temperature and above the critical pressure of these extractant compounds.

As is well-known, the critical temperature and the corresponding critical pressure of a compound are the critical values above which conversion from the gaseous to the liquid state is no longer possible. Above these values the gases in some respects behave like liquids and the invention results from the surprising discovery that the organic constituents of the reaction mixtures originating from the hydroformylation or carbonylation, including the high-boiling residues, substantially dissolve in the quasi-liquid of supercritical gas and can thus be extracted as if a true liquid was being used. By contrast, the catalysts are virtually not taken up by the supercritical gases and are almost completely left behind on extraction. The catalyst-containing residue which is left can then be directly recycled to the synthesis stage. In general, the conditions used are such that from 20 to 80 percent by weight of the high-boiling residue are removed by extraction, using the method of the invention, either together with the desired products or, if these can be distilled without detriment to the catalyst, after prior distillative removal of the products.

The Table which follows shows the approximate critical data of some of the compounds which may be used in the process of the invention.

|  | Critical temperature °C. | Critical pressure bar |
|---|---|---|
| $CO_2$ | 31 | 74 |
| Ethane | 32 | 49 |
| Ethylene | 10 | 51 |
| Propane | 97 | 47 |
| Butane | 152 | 38 |
| Isobutene | 145 | 40 |
| $CClF_3$ | 30 | 39 |

Preferred extractants are those with critical temperatures of from −50° to 200° C., especially from 0° to 150° C. The working temperatures used with these extractants are advantageously in each case from about 5° to 50° C. higher. The pressres used are preferably from 40 to 200 bar above the critical pressure. As a rule, from about 2 to 20 kg of the extractant according to the invention are required to take up 1 kg of organic substance (desired product and/or residue):

According to all our observations so far, all metal compounds, if they are non-volatile, fail to be taken up by the supercritical gases, so that the chemical nature of these compounds is immaterial in respect of their behavior during extraction. We shall therefore specifically mention merely those metal complex compounds which have hitherto attained the greatest importance in oxo synthesis processes, namely cobalt and especially rhodium complexes, eg. $Co_2(CO)_4(PR_3)_2$, $Rh_2(CO)_6(PR_3)_2$, $HCo(CO)_2(PR_3)_2$, $HCo(CO)_3(PR_3)$, $Co_2(CO)_6(PR_3)_2$ and pyridinium-$[Co(CO)_4]^-$, where the R's are identical or different hydrocarbon radicals of 4 to 16 carbon atoms. Conventional phosphine ligands are those where the radicals R are n-butyl, n-hexyl, n-octyl, n-decyl or phenyl.

Depending on their degree of enrichment, these compounds are in general present in the high-boiling residues in concentrations of from 0.01 to 3 percent by weight, expressed as metal.

As is generally known, the hydroformylation of olefinically unsaturated compounds gives, depending on the process conditions, varying amounts of aldehydes and alcohols, in addition to volatile by-products (eg. paraffinic compounds from the hydrogenation of the olefinic compounds):

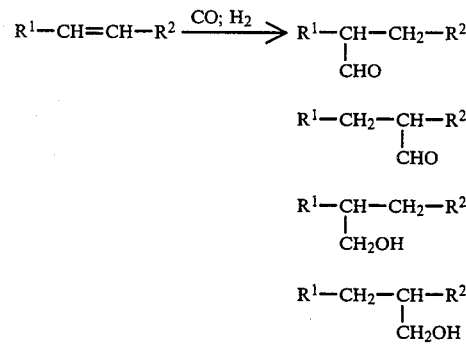

In these formulae, $R^1$ and $R^2$ are hydrogen or organic radicals.

By-products formed from these primary products are aldolization and acetalization products, and esters of acids, the acids being formed by disproportionation of the aldehydes to acids and alcohols. These by-products are of low volatility and substantially form the oxo synthesis residue under discussion.

Carbonylation in the narrower sense (it is to be noted that hydroformylation is often included in the general category of carbonylation reactions) is a similar reaction which yields acids or esters depending on whether water or an alcohol is used as the reactant in addition to carbon monoxide:

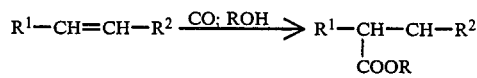

$$R^1-CH-CH-R^2$$
$$|$$
$$COOR$$

here $R^1$, $R^2$ and R are hydrogen or organic radicals.

Here again, a variety of high-boiling by-products are formed, which in their chemical nature resemble those from the hydroformylation reaction, since the carbonylation reaction also takes place in a reducing atmosphere (CO).

The process according to the invention is of particular importance in conjunction with syntheses, employing cobalt or rhodium catalysts, which are operated industrially, ie. the hydroformylation and carbonylation of ethylene, propylene and $C_8$–$C_{14}$-olefins. These processes produce from about 10 to 50 kg of high-boiling residue per tonne of the above desired products.

Where the residue is worked up, the extraction is carried out in a vertical autoclave which is advantageously filled to the extent of from 10 to 30% of its volume with the residue. The remaining volume, above the residue, is then filled with the gas under supercritical conditions. To carry out the extraction, additional gas is passed—always under the supercritical conditions—through the residue from below, and is taken off, at the rate of introduction—at the top, where it has become enriched with residue. It is not possible to specify absolute values of the optimum rate of extraction, since it depends on the nature of the residue and of the gas, as well as on the temperature, pressure and details of the apparatus. However, these values can readily be determined by starting with a low throughput of gas, increasing this throughput per unit time in stages and in each case determining the amounts of residue extracted. The optimum throughput is then the throughput at which the amount of residue no longer increases significantly if the throughput is again increased.

As in the case of normal extractions, the efficiency is increased if the extractant, ie. the gas, is finely divided, and if packings are used in order to accelerate the attainment of equilibrium.

The gas is discharged via a pressure-reducing valve into a separator, and since the gas is advantageously recycled and must, for this purpose, be re-compressed, it suffices to reduce the pressure to below the critical pressure. Hereupon, the gas loses the extracted high-boiling material, which can then be withdrawn from the separator. If the high-boiling material still contains small amounts of metal, this is as a rule due to the fact that the metal compound has not been extracted, but been mechanically entrained. However, this phenomenon can be virtually completely avoided by carrying out the extraction process more slowly. After the extraction, the raffinate phase can be directly recycled to the synthesis stage. Other compounds contained in the high-boiling material, namely excess complexing agents, such as triphenylphosphine, pass partly into the extract phase and partly into the raffinate phase.

A similar procedure is followed if, after removing the desired products by distillation, not only the residue, but the entire reaction mixture is to be worked up by the method according to the invention. Since it is true as a rule that for compounds of relatively low molecular weight a relatively low pressure of the supercritical gas suffices for the extraction, and that increasing pressures become necessary with increasing molecular weight, it is possible, by selecting an appropriate pressure, first to extract the desired products and then to extract the residue under a higher pressure. If purification of the desired products is necessary, the extraction process can be repeated, or the products can be separated from high-boiling material by conventional distillation methods.

Surprisingly, the catalysts are reactivated by treating their solutions in accordance with the invention, and thereupon show the same activity as freshly prepared catalyst. In view of the fact that the activity of the catalyst can, after several cycles of the untreated high-boiling material, decline to about 40% of its initial value, this reactivation constitutes a particular advantage of the process. In this context, a direct measure of the activity of the catalyst is the conversion of the olefin to hydroformylation products per unit time.

EXAMPLE 1

250 g of a high-boiling residue which was obtained, in the hydroformylation of propylene by means of a rhodium catalyst, after separating off the desired products (butyraldehydes and butanols) and the volatile constituents, and which contained 209 ppm of Rh (=52.3 mg of Rh) in the form of the complex $HRh(CO)(PPh_3)_3$ and 7 percent by weight of free triphenylphosphine $PPh_3$, were extracted with ethylene in the supercritical state in an autoclave of 1.5 liters capacity, at 25° C. and 100 bars, by passing 37 kg (=2.2 $m^3$ (S.T.P.)) of ethylene continuously over 10 hours through the residue from below, whilst keeping the pressure and temperature constant, and drawing off the corresponding amount via a pressure-reducing valve.

On reducing the pressure of the ethylene, 169 g (=68% by weight) of the extracted residue, containing 2.1 mg of Rh, condensed. The remainder of the residue remained in the autoclave together with 50.2 mg of Rh. Accordingly, 96% of the rhodium was recoverable, in the form of the active complex. This remaining portion of the residue was suitable for recycling, without further treatment, to the hydroformylation stage.

The effect of this treated residue on the hydroformylation reaction was compared with the effect of an equal amount of untreated residue of the same Rh concentration. It was found that the catalyst in the untreated residue initially exhibited an activity of only about 70% of the catalyst in the treated residue. The conversion of the propylene to butyraldehydes and butyl alcohols under identical hydroformylation conditions served as a measure of the activity.

EXAMPLE 2

A high pressure tube of 1.2 liters capacity was fed continuously, from below, with 135 g per hour of a high-boiling residue from the synthesis described in Example 1 and with 940 g per hour (=470 l (S.T.P.)) of carbon dioxide, the gas being at 45° C. and under a pressure of 130 bar. After reducing the pressure of the gas taken off at the top, 18 g per hour of virtually catalyst-free residue were obtained. In total, 2,050 g of high-boiling material, containing 512 mg of Rh, were treated in this way, 595 g, containing about 94% of the rhodium, were left.

EXAMPLE 3

80 g of a high-boiling residue which was obtained, in the hydroformylation of tetradec-1-ene by means of a cobalt carbonyl/trioctylphosphine catalyst, after removing the desired products (pentadecanals and pentadecanols) and the volatile constituents, and which contained 3.2 g of cobalt in the form of a complex, were extracted with ethylene, by the method described in Example 1, at 20° C. and 110 bar. This allowed 62% of the high-boiling material to be removed, and the remaining residue contained 96% of the cobalt.

The residue consisted in the main of diols, and acetals of these diols. The diols, for their part, resulted from the bis-hydroformylation of diolefins which are usually present in small amounts in tetradec-1-ene.

EXAMPLE 4

375 g of a reaction mixture which originated from the hydroformylation of octadec-1-ene by means of the $HRh(CO)(PPh_3)_3$ complex and which contains 6% by weight of octadec-1-ene, 87% by weight of nonanols, 7% by weight of free triphenylphosphine and 65 mg of rhodium were extracted with ethylene, by the method described in Example 1, at 100 bar and 27° C. The octadecene and the nonanols passed quantitatively into the extract phase, which contained only 0.6 mg of rhodium.

The catalyst-containing residue was recycled to the hydroformylation stage. The activity of the catalyst corresponded to that of a freshly added Rh complex.

EXAMPLE 5

Using the method described in Example 4, 330 g of a reaction mixture originating from the hydroformylation of tetradec-1-ene with $Co_2(CO)_4(P\text{-}octyl_3)_4$ were extracted with ethylene at 110 bar and 25° C. After releasing the pressure, 290 g of extract phase were obtained, consisting in the main of pentadecanols and pentadecanals in addition to small amounts of tetradecane, unconverted tetradecene and 2% by weight of the cobalt.

The residue which contained 98% by weight of the cobalt was recycled to the hydroformylation stage, where the catalyst proved to be fully active.

EXAMPLE 6

Using the apparatus for continuous extraction, described in Example 2, 120 g per hour of the hydroformylation mixture from Example 4 were extracted with 600 g (about 300 l (S.T.P.)) of carbon dioxide at 43° C. and 110 bar. This produced between 96 and 102 g per hour of extraction phase of the same composition in Example 4; the rhodium content of this extraction phase was only 0.4 mg.

The residue was recycled to the hydroformylation stage, where the catalyst proved fully active.

EXAMPLE 7

5,000 g of a residue which was obtained, in the carbonylation of ethylene with carbon monoxide and methanol by means of pyridinium⊕(Co(CO)₄)⊖ after removing the methyl propionate by distillation, and which contained 100 g of Co were extracted with 25 kg (about 12.5 $m^3$ (S.T.P.)) of $CO_2$ at 40° C. and 110 bar. The amount of residue thus produced was 720 g. 93 g of cobalt remained in this residue, and 7 g passed into the extract phase.

The residue was recycled to the carbonylation stage, where the catalyst proved fully active.

We claim:

1. A process for working up a reaction mixture formed in producing aldehydes and/or alcohols or acids and/or esters by the hydroformylation or carbonylation of olefins in the presence of non-volatile catalytic complex compounds of metals of group VIII of the periodic table and wherein the desired aldehydes and/or alcohols or acids and/or esters are recovered from the reaction mixture leaving behind high-boiling residue in which said non-volatile catalytic compounds are dissolved, which process comprises: contacting the reaction mixture containing non-volatile catalytic compounds dissolved in high-boiling residue with an extractant compound selected from the group consisting of carbon dioxide, a $C_2$–$C_4$-paraffin, a $C_2$–$C_4$ olefin or a normally gaseous halohydrocarbon at a temperature above the critical temperature of the extractant compound and at a pressure above the critical pressure of the extractant compound to separate high-boiling residue from the non-volatile catalyst, and thereafter returning the catalyst to the reaction mixture.

2. The process of claim 1, wherein the non-volatile catalytic complex is a compound of cobalt or rhodium.

3. The process of claim 2 wherein the process temperature is from 5° to 50° C. above the critical temperature of the extractant compound and the process pressure is from 40 to 200 bar above the critical pressure of the extractant compound.

4. The process of claim 2 wherein the low-boiling constituents of the reaction mixture and the desired products have been removed before the reaction mixture is contacted with the extractant compound.

5. The process of claim 2, wherein from 20 to 80% by weight of the high-boiling residue is separated from the non-volatile catalyst by extraction.

* * * * *